United States Patent
Hatlan et al.

(10) Patent No.: US 12,279,907 B2
(45) Date of Patent: *Apr. 22, 2025

(54) SUPPORT SYSTEM FOR A PORTABLE ULTRASOUND MACHINE

(71) Applicant: Sonivate Medical, Inc., Portland, OR (US)

(72) Inventors: James T. Hatlan, Portland, OR (US); Dan Tidwell, Portland, OR (US); Bill McDonough, Portland, OR (US)

(73) Assignee: Sonivate Medical, Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,610

(22) Filed: Aug. 14, 2023

(65) Prior Publication Data

US 2023/0380801 A1 Nov. 30, 2023

Related U.S. Application Data

(63) Continuation of application No. 16/855,259, filed on Apr. 22, 2020, now Pat. No. 11,723,623.

(51) Int. Cl.
*A47B 23/04* (2006.01)
*A61B 8/00* (2006.01)
*F16M 13/00* (2006.01)

(52) U.S. Cl.
CPC .......... *A61B 8/4209* (2013.01); *A61B 8/4427* (2013.01); *F16M 13/005* (2013.01); *A47B 23/043* (2013.01); *A63B 2213/008* (2013.01)

(58) Field of Classification Search
CPC ............... A47B 23/042; A47B 23/043; A63B 2213/008
USPC ........ 248/454, 455, 456, 460; 600/102, 131, 600/437, 446
See application file for complete search history.

(56) References Cited

U.S. PATENT DOCUMENTS

| | | | |
|---|---|---|---|
| 4,466,593 A | | 8/1984 | Odenath |
| 6,113,052 A | * | 9/2000 | Gentile ................ A47B 23/043 248/456 |
| 8,162,823 B2 | | 4/2012 | Suzuki |
| 9,298,351 B2 | | 3/2016 | Sato |
| 9,847,002 B2 | | 12/2017 | Kiani et al. |
| 11,723,623 B2 | * | 8/2023 | Hatlan ................... F16M 11/10 248/672 |
| 2015/0289841 A1 | | 10/2015 | Brusaca et al. |
| 2018/0000319 A1 | | 1/2018 | Rutschmann et al. |
| 2019/0298057 A1 | | 10/2019 | Xiao et al. |
| 2020/0288861 A1 | | 9/2020 | Chang |

* cited by examiner

*Primary Examiner* — Alfred J Wujciak
(74) *Attorney, Agent, or Firm* — K&L Gates LLP

(57) ABSTRACT

A support system for a portable ultrasound machine is disclosed. The example support system includes a carrier for an imaging display and a bracket for a beamformer. The bracket mechanically couples to the carrier in a plurality of positions depending on a desired use of an operator of the portable ultrasound machine.

7 Claims, 8 Drawing Sheets

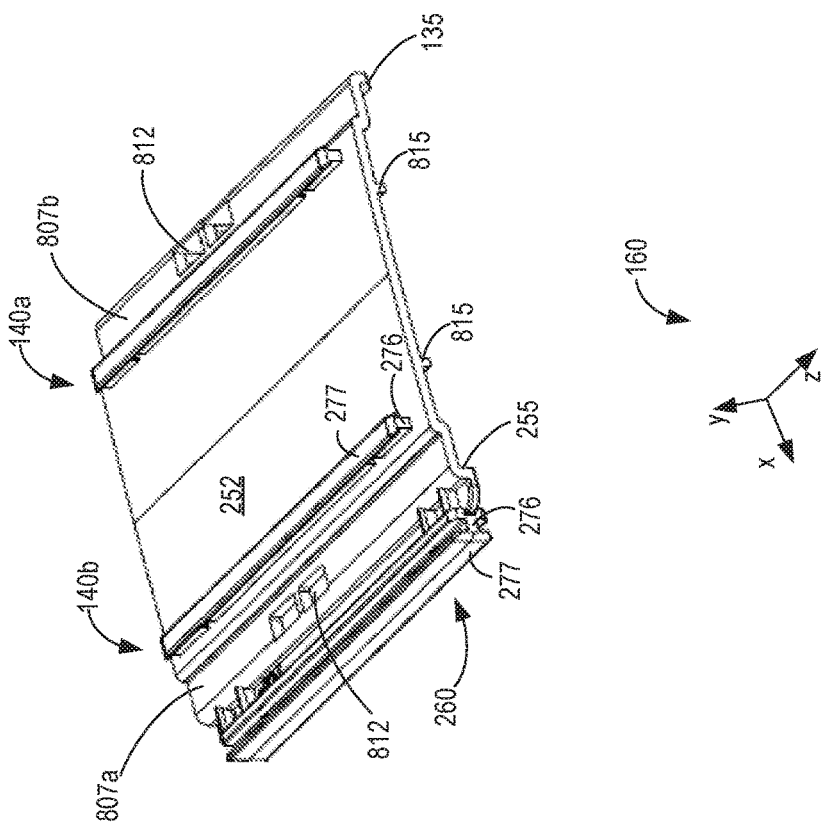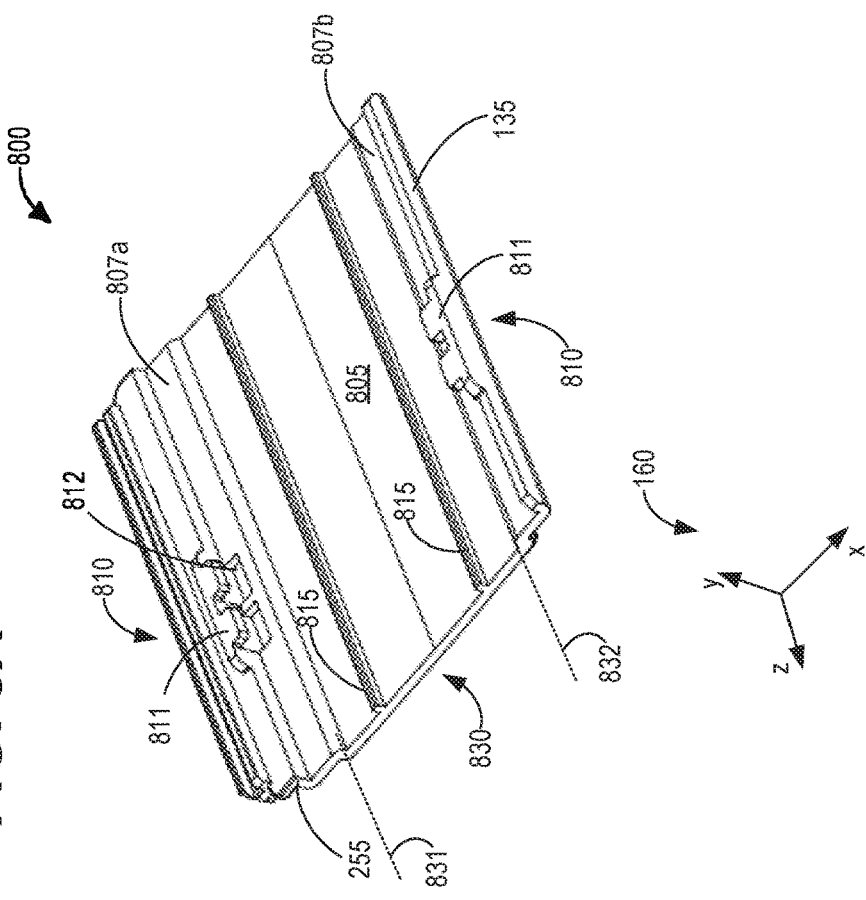

SUPPORT SYSTEM FOR A PORTABLE ULTRASOUND MACHINE

PRIORITY CLAIM

This application is a continuation of U.S. Non-Provisional patent application Ser. No. 16/855,259, filed Apr. 22, 2020, now U.S. Pat. No. 11,723,623, the entire disclosure of which is hereby incorporated by reference.

TECHNICAL FIELD

Embodiments herein relate to the field of ultrasound imaging, and, more specifically, to a bracket and carrier system for assistance in performing portable ultrasound imaging.

BACKGROUND

Medical ultrasound imaging has become an industry standard for many medical imaging applications. In some examples, an ultrasound imaging system includes at least one ultrasound probe/transducer, an input device such as a keyboard, a computer, and a display. The ultrasound probe/transducer generates ultrasound waves that can penetrate tissue, and receives ultrasound waves reflected back from the tissue. System inputs to the computer are communicated via the keyboard (or other input device such as a knob), and images of tissue structures are visualized on the display.

However, ultrasound imaging systems such as those described above can be bulky, and thus may not be readily amenable to portable use in hospital and/or field environments. Accordingly, in recent years there has been an increase in medical ultrasound imaging equipment that is portable, thereby allowing medical personnel to easily transport the equipment to and from hospital and/or field locations. Such portable ultrasound systems are the result of advances in the underlying technology, permitting miniaturization of the necessary electronics. This, in turn, has reduced the size and weight of such portable systems. Additionally, the appearance of touch screen technology has enabled many input and control functions to be designed for use with touch screen technology.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 8A illustrates an isolated top view of the bracket of the portable ultrasound machine support system of FIG. 1, according to an embodiment;

FIG. 8B illustrates an isolated bottom view of the bracket of the portable ultrasound machine support system of FIG. 1, according to an embodiment.

DETAILED DESCRIPTION OF DISCLOSED EMBODIMENTS

Figure 1:
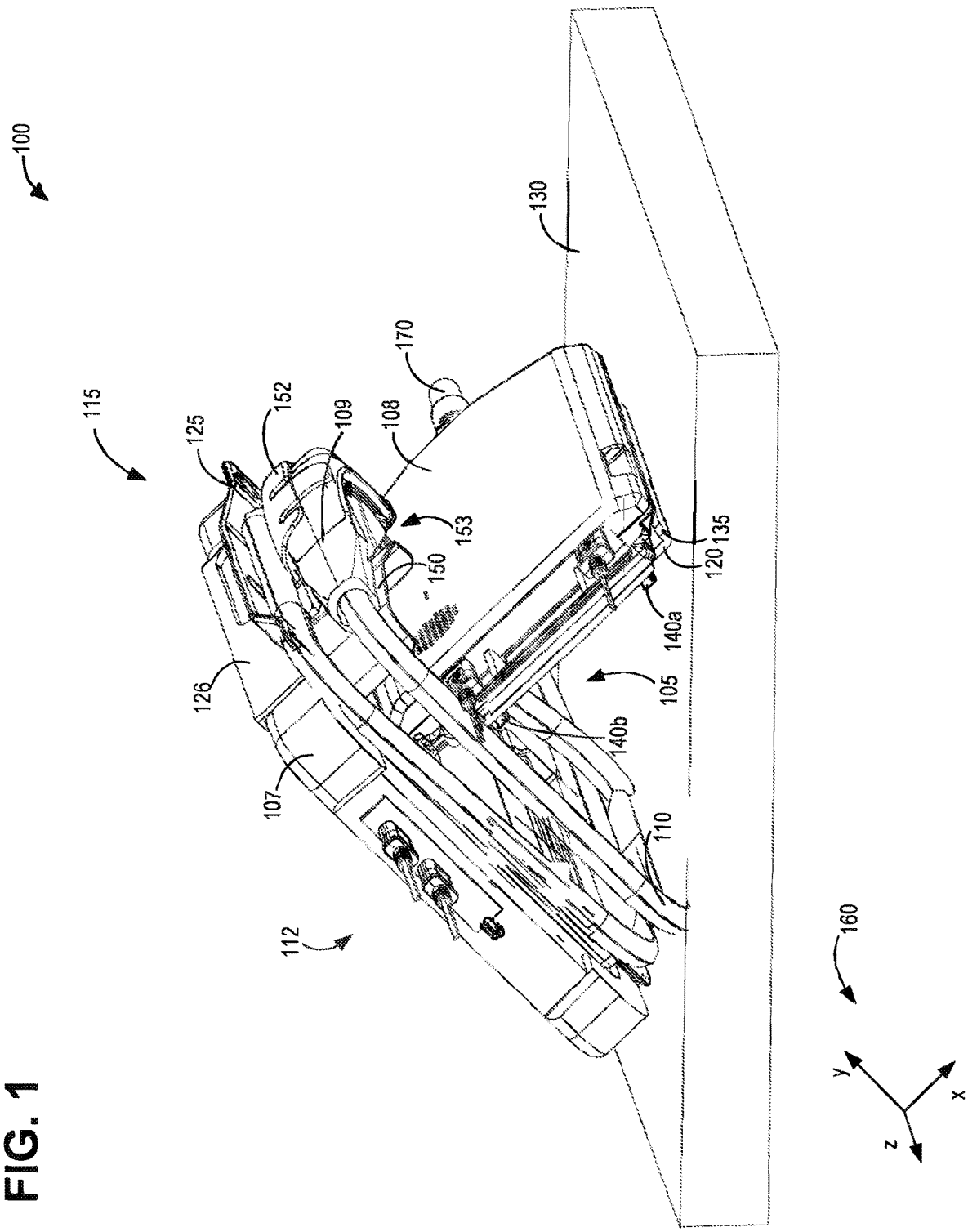
FIG. 1 illustrates an example portable ultrasound machine support system, for use with a portable ultrasound machine, according to an embodiment.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

The description may use the terms "substantially", which may refer to something being within essentially the same as something else, with minor deviations encompassed, but can also include something being exactly the same, or not different than, something else.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Portable and handheld ultrasound devices are being used increasingly in clinical practice. Their use is considered of particular importance in situations where time is of the essence (e.g., emergency room, intensive care), or where the location (e.g., remote locations, doctor's office, etc.) favors a portable device over larger conventional devices. Portable ultrasound devices are typically light in weight, small and durable, while also providing high quality, high-resolution imaging, in many examples at a lower cost than traditional ultrasound systems.

However, use of portable and handheld ultrasound imaging systems can be challenging given the nature of the small size and mobile aspects of components comprising such systems. As one example, it may be challenging to both hold an imaging display and operate an ultrasound probe, particularly in a case where any adjustments are desired, as both hands of an operator may already be in use. Making adjustments thus would require the user to put down the display and/or probe to free a hand, which may interrupt any procedure in process with the system or require an additional person. Furthermore, it is increasingly common for portable ultrasound imaging systems to include touchscreen displays, which nevertheless can present similar challenges, requiring a free hand to interact with the touchscreen display. In fact, such challenges may even be exacerbated because the act of touching the screen may cause movement of the screen, resulting in the screen not being readily viewable and/or being positioned in a manner not readily accessible to an operator that is also operating a probe on a particular region of a body. The inventors herein have recognized the above-mentioned issues, and have developed systems and apparatuses to address them.

Accordingly, embodiments herein provide for a support system for a portable ultrasound machine comprising a carrier and a bracket, where the bracket is capable of coupling to the carrier in one of a first position, a second position and a third position. Specifically, the carrier may have an outer face and an inner face, the inner face including a handle protruding therefrom, the inner face further including a first carrier connector positioned below the handle and a second carrier connector positioned below the first carrier connector. The bracket may be for supporting a beamformer, and may have a top-side and a bottom-side, and may include a base area, a first shelf and a second shelf flanking the base area, an inner lip stemming from the first shelf and an outer lip stemming from the second shelf. The bracket may further include a first bracket connector protruding from the bottom-side of the base area adjacent the outer lip, a second bracket connector protruding from the bottom-side of the base area adjacent the inner lip, and a third bracket connector protruding laterally from the inner lip in a direction away from the base area of the bracket. As mentioned, the bracket may couple to the carrier in the first position, the second position, or a third position. The first position may include the third bracket connector connected to the first carrier connector, the second position may include the third bracket connector connected to the second carrier connector, and the third position may include both the first bracket connector connected to the first carrier connector and the second bracket connector connected to the second carrier connector.

In one example of such a support system, the base area of the bracket may be perpendicular to the inner face of the carrier in the first position and the second position, and the base area of the bracket may be parallel to the inner face of the carrier in the third position.

As another example of the support system, in the first position the carrier may adopt a first angle and the bracket may adopt a second angle with respect to a vertical axis that is perpendicular to a surface, under conditions where a bottom edge of the carrier and an outer edge of the bracket are both in physical contact with the surface. In the second position the carrier may adopt a third angle and the bracket may adopt a fourth angle with respect to the vertical axis under conditions where the bottom edge of the carrier and the outer edge of the bracket are both in physical contact with the surface. In the above examples the first angle may be greater than the third angle and the fourth angle may be greater than the second angle.

In another example of the support system the carrier may further comprise a first hook and a second hook each protruding away from the outer face of the carrier, the first hook and the second hook operable for slidingly receiving an imaging display of the portable ultrasound machine. In some examples the support system may include a probe holder protruding from the inner face of the carrier adjacent the handle, the probe holder and at least a portion of an upper side of the handle may be operational to secure a probe of the portable ultrasound machine. In yet another example the support system may include a ridge of the carrier adjacent a top-portion of the probe holder and just above the handle and the first hook, the ridge may be of a shape that creates a groove between the probe holder and the ridge, and the groove may be operational to receive at least a portion of a probe cable of the portable ultrasound machine.

In another example of the support system, the support system may further comprise a first fastener integrated into the inner lip and the first shelf, and a second fastener integrated into the outer lip and the second shelf. The first fastener and the second fastener may be for securing the beamformer to the top side of the bracket.

Another example discussed herein includes an apparatus for a portable ultrasound machine. The apparatus may comprise a carrier having an outer face and an inner face. A first hook may extend from the outer face just below an upper edge of the carrier and a second hook may extend from the outer face adjacent a lower edge of the carrier. The first hook and the second hook may be for receiving a computing device of the portable ultrasound machine, for example. A probe holder may extend from the inner face, at a position approximately opposite the first hook relative to a height of the carrier. The probe holder may be for at least partially immobilizing and protecting a probe of the portable ultrasound machine. A carrier handle may extend from the inner face adjacent the probe holder with respect to a width of the carrier. A first mechanical connector may be associated with the inner face and positioned below the probe holder, and a second mechanical connector may be associated with the inner face and positioned below the first carrier connector. Each of the first and the second mechanical connectors may be configured for attachment of a bracket thereto.

In one example of such an apparatus, each of the first mechanical connector and the second mechanical connector may be female connectors. In one such an example, the first mechanical connector may include a first track and the second mechanical connector may include a second track, wherein the first track and the second track may be parallel to one another and parallel to the lower edge of the carrier.

In another example of such an apparatus, the apparatus may further comprise a ridge of the carrier that extends along a top side of the first hook. The ridge may be tapered on either end of the ridge, and the tapering may render the ridge of the carrier concave on the inner face and convex on the outer face. In such an example, the ridge may create a groove between a portion of the probe holder and the ridge. The groove may be capable of receiving a segment of a probe cable of the portable ultrasound machine, in some examples.

In another example of such an apparatus, the probe holder may further comprise an upper holder section and a lower holder section. The upper holder section may include a first finger and a second finger each extending away from the inner face of the carrier. The first finger may be substantially perpendicular to the second finger. In such an example, the lower holder section may include a third finger that extends away from the inner face of the carrier. The third finger may be angled with respect to each of the first finger and the second finger. Each of the first finger, the second finger and the third finger may extend away from the inner face of the carrier to a substantially same extent, in some examples. In some examples, the first finger may have a slight curvature and additionally or alternatively may be flexible with respect to the upper holder section of the probe holder. The probe holder may be affixed to the inner face of the carrier by one or more probe holder fasteners, or other relevant means known to those of ordinary skill in the art. In some examples the lower holder section may further comprise a probe holder base that stems from the third finger along the inner face of the carrier. The probe holder base may extend away from the inner face of the carrier to a lesser extent than the first finger, the second finger and the third finger, in some examples.

In another example of such an apparatus, the carrier handle may extend from the inner face of the carrier just below the ridge and may be substantially of a c-shape. At least a portion of the carrier handle may serve as a support structure for the probe of the ultrasound machine, in some examples.

Another example of an apparatus for a portable ultrasound machine as discussed herein may comprise a bracket for supporting a beamformer of the portable ultrasound machine. The bracket may include a top side and a bottom side, and a first shelf and a second shelf extending from and flanking a base area of the bracket. The first shelf and the second shelf may each adopt an elevated position with respect to the top side of the base area. The apparatus may further include an inner lip extending from the first shelf and an outer lip extending from the second shelf. The inner lip may be substantially perpendicular to the first shelf and the outer lip may be substantially perpendicular to the second shelf. Each of the inner lip and the outer lip may further be elevated with respect to the top side of the base area. The apparatus may further include one or more bottom side bracket connectors protruding from the bottom side of the base area, and one or more lateral bracket connectors protruding from the inner lip.

In an example of such an apparatus, the apparatus may further comprise a first fastener integrated into the inner lip and the first shelf. The first fastener may include a first set of teeth extending from the inner lip, and a first set of notches included in the first shelf. The first set of notches may be positioned directly underneath the first set of teeth, in some examples. The apparatus may further include a second fastener integrated into the outer lip and the second shelf. The second fastener may include a second set of teeth extending from the outer lip, and a second set of notches included in the second shelf. The second set of notches may be positioned directly underneath the second set of teeth. The apparatus may include one or more ridges extending from the top side of the base area of the bracket. A height of the one or more ridges may be in a substantially same plane as the first shelf and the second shelf, in some examples.

In another example of such an apparatus, the one or more bottom side bracket connectors may further comprise a first connector protruding from the bottom side of the bracket adjacent the outer lip and extending along the bottom-side of the base area parallel to each of the inner lip and the outer lip. The apparatus may include a second connector protruding from the bottom-side of the bracket adjacent the inner lip and extending along the bottom side of the base area parallel to each of the inner lip and the outer lip. In some examples, each of the first connector and the second connector may have a general t-shape (e.g., shaped like the letter T).

In another example of such an apparatus, the one or more lateral bracket connectors may further comprise a third connector protruding laterally from the inner lip in a direction away from the base area of the bracket. The third connector may extend along an outer portion of the inner lip and may have the general t-shape. In such an example, each of the first connector, the second connector and the third connector may have a substantially same set of dimensions. The third connector may be substantially perpendicular to each of the first connector and the second connector, in some examples.

Turning now to the Figures, FIG. 1 shows an example illustration 100 of a portable ultrasound machine support system 105. Portable ultrasound machine support system 105 may also be referred to herein as an ultrasound support system, or simply, a support system. In embodiments, support system 105 functions to support, position and/or secure at least computing device 107 (also referred to herein as acomputing device, an interactive imaging display device, imaging device, or imaging display device), beamformer 108, probe 109, and probe cable 110. Discussed herein, components including but not limited to computing device 107, beamformer 108, probe 109 and probe housing 110 may be understood to comprise ultrasound machine 112. Accordingly, support system 105 may function to support, position and/or secure various components of ultrasound machine 112. Furthermore, as discussed herein, components including but not limited to support system 105 and ultrasound machine 112 may be referred to as portable ultrasound machine system 115.

Support system 105, in embodiments, includes at least bracket 120 and carrier 125. Bracket 120 may function as a supporting structure for beamformer 108, and also may couple to carrier 125 at one or more sites of carrier 125. As will be discussed in further detail below, in one example, bracket 120 can be releasably coupled to carrier 125 at a first site and not a second site. Such an example is referred to herein as a situation in which the bracket 120 is coupled to the carrier 125 in a first position. In another example, bracket 120 can be releasably coupled to carrier 125 at the second site but not at the first site. Such an example is referred to herein as a situation in which the bracket 120 is coupled to the carrier 125 in a second position. In still another example, bracket 120 can be releasably coupled to carrier 125 at both the first site and the second site at the same time. Such an example is referred to herein as a situation in which the bracket 120 is coupled to the carrier 125 in a third position.

In embodiments, carrier 125 functions as a supporting structure for computing device 107. Specifically, carrier 125 may include a plurality of hooks 126 (one of which is visible at FIG. 1) that function to hold or secure computing device 107 (e.g., tablet, etc.) to carrier 125. With regard to reference axes 160, it may be understood that a height of carrier 125 is referenced along the y-axes. There may be one hook at a top of carrier 125 as shown at FIG. 1, and another hook at a bottom of carrier 125 (not visible at FIG. 1), for example, however other positioning of the hooks 126 with respect to carrier 125 are within the scope of this disclosure. In some examples, hooks 126 may be rigid or inflexible. In such an example, computing device 107 may be secured to carrier 125 by sliding computing device 107 between the plurality of hooks 126. In another example, hooks 126 may be flexible, whereby computing device 107 may be secured to carrier 125 by bending or otherwise deforming the hooks to receive computing device 107, after which the hooks may return to an original position (prior to the bending or deforming) thereby securing computing device 107 to carrier 125.

It may be understood that computing device 107 may comprise a tablet, smartphone, dedicated terminal, etc., or another device that can be suitably configured for use with ultrasound machine 112. Computing device 107 may have a screen or display, which in some examples may be both an input and output device (e.g., touchscreen). As discussed, in embodiments carrier 125 couples to bracket 120 by way of the first position, second position, or the third position. As will be elaborated in further detail below, depending on the position by which bracket 120 couples to carrier 125, computing device 107 may be positioned at a more vertical position with respect to a surface, such as surface 130, or a less vertical position with respect to the surface upon which supporting structure 105 (and associated ultrasound machine 112) sits. The difference in vertical position may be advantageous in that a user may be able to adjust a viewing angle of the display to their liking depending on the situation.

Bracket 120 may have a first, or outer, lip 135, and a second, or inner, lip (not visible at FIG. 1). Specifically, with regard to reference axes 160 at FIG. 1, outer lip 135 may be further from carrier 125 along the x axis, and the inner lip may be closer to carrier 125 with regard to the x axis. Each of the first outer lip and the second inner lip may function to at least partially hold beamformer 108 in place. As one example, outer lip 135 may at least partially contribute to preventing beamformer 108 from sliding off of bracket 120 as a result of gravity, when bracket 120 is positioned at an angle with respect to surface 130, as illustrated at FIG. 1. In other additional or alternative examples, the inner and outer lips may function to hold or secure beamformer 108 in place as ultrasound machine system 115 is moved around or otherwise manipulated. In the depicted embodiment, outer lip 135 is shown in physical contact with surface 130. In this way, bracket 120, by way of the physical contact with surface 130, serves to support carrier 125 and computing device 107 against gravity.

As will be elaborated in greater detail below, in embodiments bracket 120 has one or more bracket connector elements (also referred to herein as bracket connector(s)) positioned lateral to the second inner lip along the x axis, which function to mechanically couple bracket 120 to carrier 125 by way of one or more carrier connector elements (also referred to herein as carrier connector(s)) (not visible at FIG. 1), included as part of carrier 125. In some examples, the bracket connector(s) may comprise male connector components, and the carrier connector(s) may comprise female connector components. However, in other examples the bracket connector(s) may comprise female connector components, and the carrier connector(s) may comprise male connector components, without departing from the scope of this disclosure. It may be understood that FIG. 1 depicts a situation where bracket 120 is coupled to carrier 120 at the first site but not the second site, and thus it may be understood that bracket 120 is coupled to carrier 125 in the first position.

In the embodiment illustrated at FIG. 1, bracket 120 additionally includes first bracket connector 140a and second bracket connector 140b, each positioned on a bottom side of bracket 120 opposite where beamformer 108 sits, with respect to the y axis. In this example embodiment at FIG. 1, each of bracket connector 140a and bracket connector 140b may be understood to comprise male track connector elements that protrude from the bottom side of bracket 120, and which extend along the bottom side of bracket 120 along the z axis. While not explicitly illustrated at FIG. 1, in an example where carrier 125 includes a plurality (e.g., 2) of female track connector elements designed to, for example, slidably receive each of bracket connector 140a and 140b, it may be understood that bracket 120 may be coupled to carrier 125 at both the first site and the second site when each of bracket connector 140a and 140b are engaged with the plurality of female track connector elements associated with carrier 125. As discussed, the example of FIG. 1 depicts a situation where bracket 120 is coupled to carrier 125 at the first site but not the second site, by way of the bracket connector element(s) positioned laterally with respect to the second inner lip along the x axis, which is not visible at FIG. 1 but which will be elaborated in greater detail below.

Carrier 125 may additionally include carrier handle 150 and probe holder 152. Probe holder 152 may define at least part of a probe pocket 153 for receiving and protecting the probe 109, for securing probe 109 to carrier 152 when probe 109 is not in use. At least a portion of probe 109 may rest upon or be at least in some physical contact with carrier handle 150. In some examples, handle 150 may be tapered at a first and/or second end of handle 150 (the first and second end discussed in relation to the z axis), to accommodate a general shape of probe 109 and accompanying probe cable 110. It may be understood that probe cable 110 may releasably couple to beamformer 108 by way of probe cable attachment connector 170.

Figure 2B:
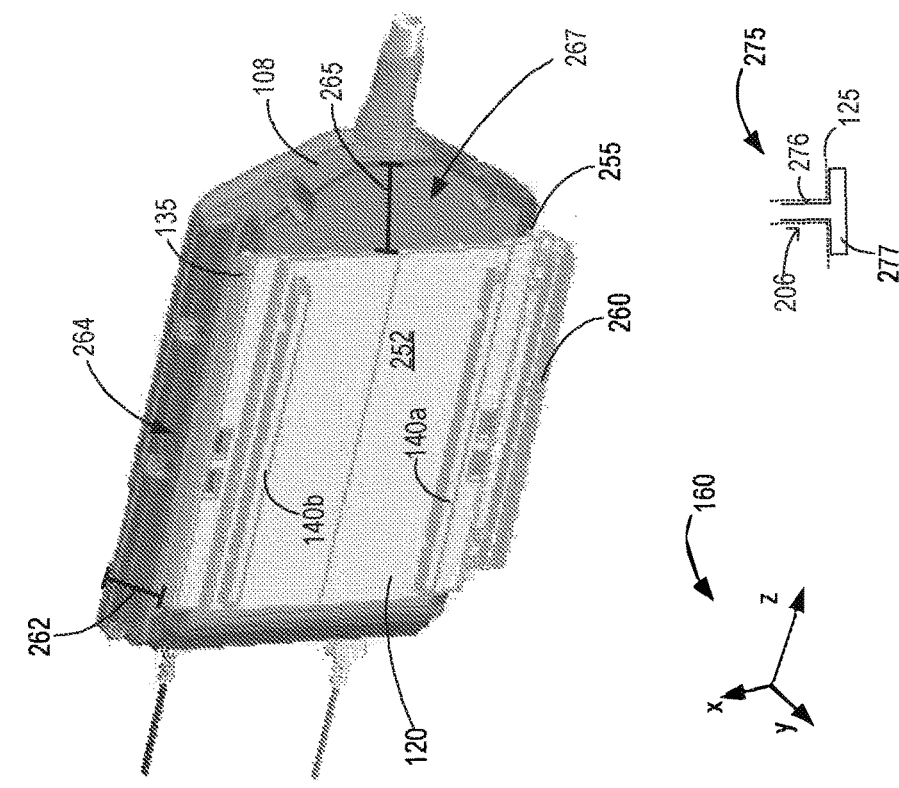
FIG. 2B illustrates a bracket of the portable ultrasound machine support system of FIG. 1 coupled to a beamformer, according to an embodiment.
Figure 2A:
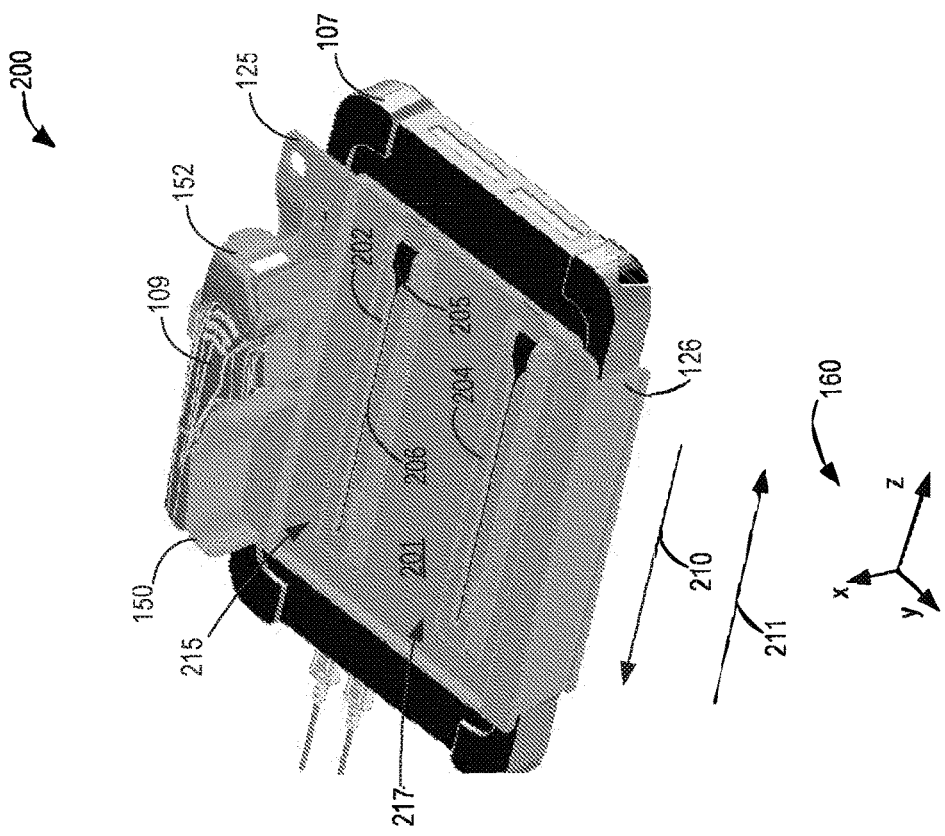
FIG. 2A illustrates a carrier of the portable ultrasound machine support system of FIG. 1, coupled to a computing device, for example a tablet, according to an embodiment.

Turning to FIG. 2A, depicted is an isolated image 200 of the example carrier 125 coupled to computing device 107, shown with the same reference axes 160 as that discussed with regard to FIG. 1. As discussed herein, the view at FIG. 2A illustrates an inner face 201 of carrier 125. It may be understood that opposite the inner face of carrier 125 is an outer face (not shown) of carrier 125, in embodiments. The view of carrier 125 at FIG. 2A illustrates hook 126 positioned at the bottom of carrier 125, and not visible at FIG. 2A is another hook which may be positioned at the top of carrier 125 (refer to FIG. 1). Shown also is probe 109, a portion of which may be received by probe holder 152 and a portion of which may extend along a top portion of carrier handle 150. Depicted are two carrier connectors, specifically first carrier connector 202 and second carrier connector 204. In this example embodiment depicted at FIG. 2A, first carrier connector 202 and second carrier connector 204 represent female carrier connectors, each of which function to receive male bracket connectors (e.g., bracket connector 140a and 140b at FIG. 1). Each of first carrier connector 202 and second carrier connector 204 may include a receiving opening 205 of a larger cross-sectional area that tapers into a slit opening 206 of smaller cross-sectional area than receiving opening 205. The larger cross-sectional area of opening 205 may enable the bracket connector(s) to be slidingly received, and subsequently the bracket connector(s) may be slid along the z axis in the direction of arrow 210 by way of slit opening 206 to secure the bracket connector and bracket (e.g., bracket 120 at FIG. 1) to carrier 125. Said another way, the embodiment illustrated at FIG. 2A shows an example where carrier connectors (e.g., carrier connector 202 and carrier connector 204) comprise female track connectors, designed to receive male track connectors (examples of which are further discussed below). With reference to FIG. 1, it may be understood that each of bracket connector 140a and bracket connector 140b may simultaneously be slidingly engaged with the female track connectors 202 and 204 shown at FIG. 2, to secure bracket 120 to carrier 125 at both the first female carrier connector 202 and the second female carrier connector 204. Discussed herein it may be understood that, in embodiments, the first carrier connector 202 corresponds to first site 215 and second carrier connector 204 corresponds to second site 217. In order to release bracket 120 from carrier 125, it may be understood that bracket 120 and corresponding bracket connector(s) may be slid in or moved in the opposite direction as that depicted by arrow 210, represented at FIG. 2A by arrow 211.

Turning now to FIG. 2B, depicted is an illustration 250, showing example bracket 120 when viewed from a bottom-side 252, depicted with regard to the same axes 160 as that discussed with regard to FIG. 1. Also depicted for reference is beamformer 108. Bracket 120, in embodiments, includes first outer lip 135, and also a second inner lip 255. FIG. 2A depicts in greater detail bracket connector 140a and 140b, which, in the depicted example, extend along bottom-side 252 of bracket 120 along the z axis (refer to inset 160). Also shown is bracket connector 260, which, in the depicted example, is positioned laterally to second inner lip 255 with respect to the x axis. Discussed herein, bracket connector 140a is also referred to as first bracket connector 140a, bracket connector 140b is also referred to as second bracket connector 140b, and bracket connector 260 is also referred to as third bracket connector 260. Inset 275 shows a general shape of each of the bracket connectors depicted at FIG. 2B, according to some embodiments. Specifically, each example bracket connector is in the general shape of a "T" (e.g., t-shape), with a first connector portion 276 and a second connector portion 277. It may be understood that, where the bracket connector is a general T-shape, second connector portion 277 may be any shape that conforms to the general T-shape configuration. For exemplary purposes, top portion 277 may be circular. With reference to the embodiment depicted in FIG. 2A, it may be understood that the first connector portion 276 slides through a slit (e.g., slit 206 at FIG. 2A) of a carrier connector (e.g., female carrier connector 202, 204 at FIG. 2A) while the second connector portion 277 slides behind the slit, or in other words in a space between the carrier (e.g., carrier 125 at FIG. 2A) and the computing device (e.g., computing device 107 at FIG. 2A). Dashed lines at inset 275 correspond to a portion of carrier 125, including slit 206. In the depicted embodiment, second connector portion 277 cannot fit through slit 206 due to the dimensions of second connector portion being greater than slit 206, and in this way bracket 120 may be connected/secured to carrier 125.

Bracket 120 may be of a sizing with respect to beamformer 108 such that a portion of beamformer 108 extends past outer lip 135 of bracket 120 along the x axis (refer to inset 160), as depicted illustratively by line 262. The portion of bracket 120 that extends past outer lip 135 may comprise a first groove 264, shaped generally in a shape corresponding to the probe cable (e.g., probe cable 110 at FIG. 1). As will be elaborated below, such a first groove may serve to enable the probe cable to be coiled in a manner that enables compact placement of the probe cable for storage or carrying purposes, when desired. While the embodiment at FIG. 2B depicts at least a portion of beamformer extending past outer lip 135 of bracket 120, in other examples it may be understood that the first groove may be similarly formed in a manner whereby the beamformer does not extend past outer lip 135.

Bracket 120 may be of a further sizing with respect to beamformer 108 such that another portion of beamformer 108 extends past an edge of bracket 120, along the z axis, as depicted illustratively by line 265. As will be elaborated in greater detail below, this portion in relation to the inner face (e.g., inner face 201 at FIG. 2A) of carrier 125 may define a second groove 267 which may be additionally relied upon for enabling probe cable 110 to be coiled in a manner that enables compact placement of the probe cable for storage or carrying purposes.

Figure 3A:
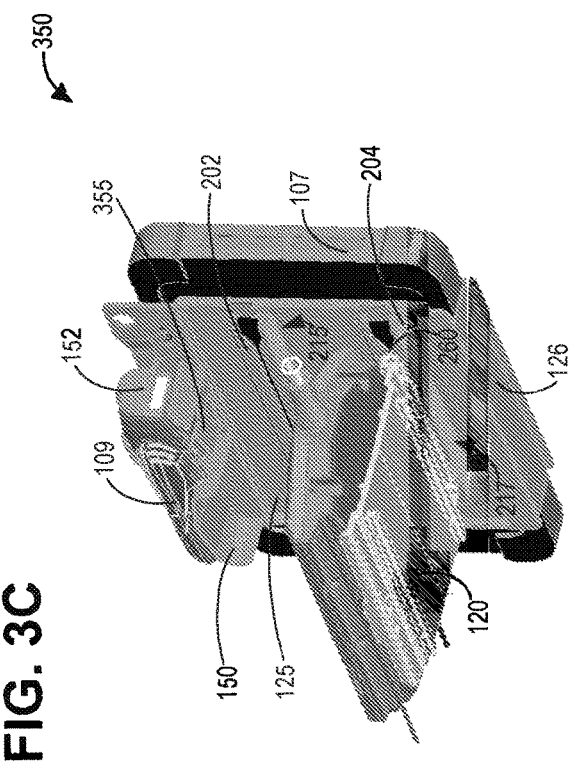
FIG. 3A illustrates an example first configuration of the portable ultrasound machine support system of FIG. 1 with the bracket coupled to the carrier in a first position, according to an embodiment.

Turning to FIG. 3A, depicted is example illustration 300, showing an example circumstance where bracket 120 is coupled to carrier 125 at first site 215 and not second site 217. In embodiments, third bracket connector 260 is engaged with first female carrier connector 202, and second female carrier connector 204 has no physical interaction with any portion of bracket 120. When bracket 120 is coupled to carrier 125 at the first site, as discussed above bracket 120 may be in the first position. As depicted, when bracket 120 is in the first position, bracket 120 (and beamformer 108, when attached), may be closer to a top of carrier 125, or in other words, closer to carrier handle (e.g., carrier handle 150 at FIG. 1) and probe holder 152, as compared to when bracket 120 is in the second position, discussed in further detail below with regard to FIG. 3C. In this example illustration 300, bracket 120 is depicted as supporting beamformer 108, and probe 109 is depicted as being positioned in probe holder 152, in embodiments. Further depicted in the example embodiment is computing device 107, secured to carrier 125 via hooks 126 (one of which is shown at FIG. 3A), as discussed above.

Figure 3B:
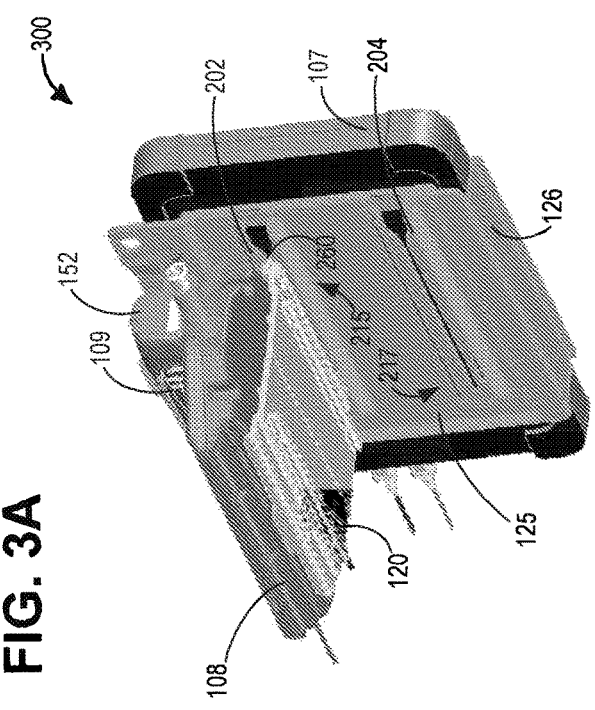
FIG. 3B illustrates the first configuration of the portable ultrasound machine support system of FIG. 3A on a surface, with the bracket coupled to the carrier in the first position, according to an embodiment.

FIG. 3B shows an example illustration 325, depicting an example of how portable ultrasound machine support system 105 supports and positions portable ultrasound machine 112 on surface 130, under circumstances where bracket 120 is in the first position, or in other words, when the third bracket connector (e.g., third bracket connector 260 at FIG. 3A) is coupled to carrier 125 at the first site (e.g., first site 215 at FIG. 3A). FIG. 3A is substantially similar to FIG. 1, and thus exhaustive description is not reiterated here for brevity. Briefly, depicted at FIG. 3B is beamformer 108, which may be supported by bracket 120, and computing device 107 which may be secured to carrier 125 via hooks 126, two of which are visible in the view (refer to common reference axes at inset 160) depicted at FIG. 3B. Further depicted at FIG. 3B is probe 109. Inset 340 depicts an angular relationship, in various embodiments, of each of carrier 125 (and computing device 107) and bracket 120 (and beamformer 108) with respect to a vertical axis 342 that is perpendicular to surface 130, under conditions where bracket 120 is mechanically coupled to carrier 125 at the first site, or in other words, when bracket 120 is in the first position as discussed herein. As shown at inset 340, carrier 125 may be at a first angle ($\theta_1$) with respect to vertical axis 342, and bracket 120 may be at a second angle ($\theta_2$) with respect to vertical axis 342.

Figure 3C:
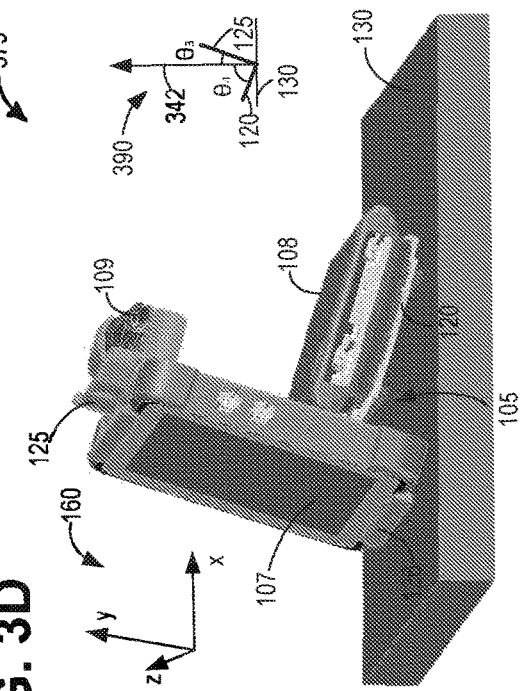
FIG. 3C illustrates an example second configuration of the portable ultrasound machine support system of FIG. 1 with the bracket coupled to the carrier in a second position, according to an embodiment.

Turning now to FIG. 3C, depicted is an example illustration 350, showing an example of a circumstance where bracket 120 is coupled to carrier 125 at second site 217 and not first site 215. Thus, in embodiments, third bracket connector 260 is engaged with second female carrier connector 204, and first female carrier connector 202 has no physical interaction with any portion of bracket 120. When bracket 120 is coupled to carrier 125 at the second site, as discussed above bracket 120 may be in the second position. As depicted, when bracket 120 is in the second position, bracket 120 (and beamformer 108, when attached) may be farther from a top of carrier 120, or in other words, farther from carrier handle 150 and probe holder 152, as compared to when bracket 120 is in the first position (refer to FIG. 3A). In this example illustration 350, bracket 120 is depicted as supporting beamformer 108, and probe 109 is depicted as being depicted in probe holder 152. Further depicted is computing device 107, which may secure to carrier 125 via hooks 126, one of which is visible at FIG. 3C. Also viewable at FIG. 3C is base area 355 of probe holder 152, which may be understood to be functional for supporting probe 109 against gravity, for example.

Figure 3D:
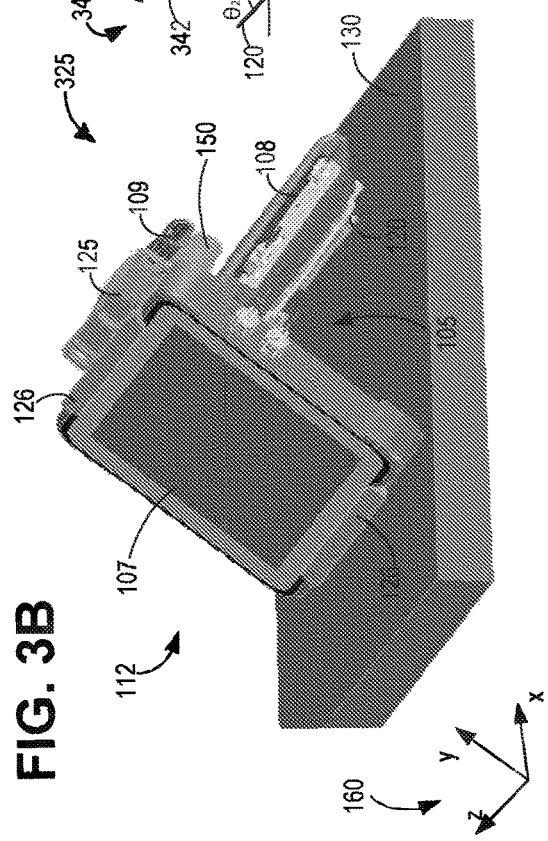
FIG. 3D illustrates the second configuration of the portable ultrasound machine support system of FIG. 3C on a surface, with the bracket coupled to the carrier in the second position, according to an embodiment.

FIG. 3D shows an example illustration 375, depicting a possible embodiment of how portable ultrasound machine support system 105 supports and positions portable ultrasound machine 112 on surface 130, under circumstances where bracket 120 is in the second position, or in other words, when the third bracket connector (e.g., third bracket connector 260 at FIG. 3C) is coupled to carrier 125 at the second site (e.g., second site 217 at FIG. 3C). Briefly, in the example depicted at FIG. 3D, is beamformer 108 supported by bracket 120, and computing device 107 which is secured to carrier 125 via hooks 126, two of which are visible in the view (refer to common reference axes at inset 160) depicted at FIG. 3B. Further depicted at FIG. 3B is probe 109. Inset 390 depicts one possible angular relationship of each of carrier 125 (and computing device 107) and bracket 120 (and beamformer 108) with respect to vertical axis 342 that is perpendicular to surface 130, under conditions where bracket 120 is mechanically coupled to carrier 125 at the second site, or in other words, when bracket 120 is in the second position as discussed herein. As shown in the example of inset 390, carrier 125 is at a third angle ($\theta_3$) with respect to vertical axis 342, and bracket 120 is at a fourth angle ($\theta_4$) with respect to vertical axis 342.

Comparison of the angular relationships depicted in the examples at each of inset 340 at FIG. 3B and inset 390 at FIG. 3D illustrates carrier 125 may be at a greater angle with respect to the vertical axis 342 when bracket 120 is in the first position, as compared to when bracket 120 is in the second position (e.g., $\theta_1 > \theta_3$). Additionally, such comparison illustrates that bracket 120 may be at a greater angle with respect to the vertical axis 342 when bracket 120 is in the second position, as compared to when bracket 120 is in the first position (e.g., $\theta_4 > \theta_2$).

Figure 4B:
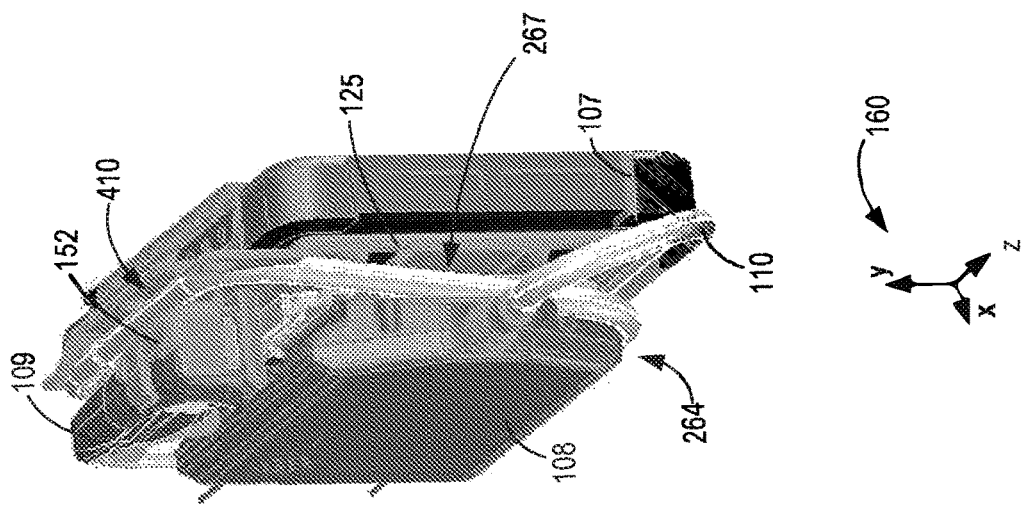
FIG. 4B illustrates the embodiment of FIG. 4A from another perspective view.
Figure 4A:
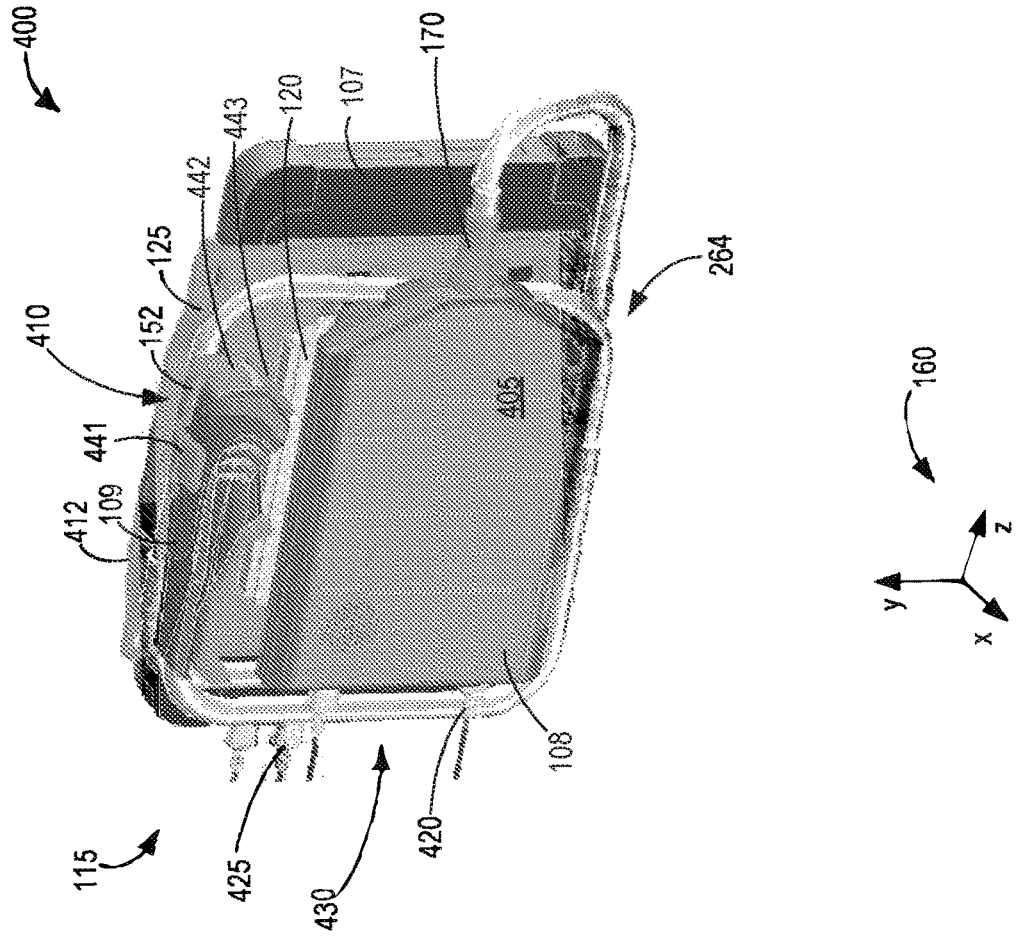
FIG. 4A illustrates the portable ultrasound machine support system of FIG. 1, with the bracket coupled to the carrier in a third position, according to an embodiment.

Turning now to FIG. 4A, depicted is example illustration 400 showing a possible embodiment where bracket 120 is coupled to carrier 125 in the third position. In such an example, bracket 120 and beamformer 108 may be understood to be substantially parallel to carrier 125, as opposed to other circumstances where bracket 120 and beamformer 108 may be substantially perpendicular to carrier 125 (e.g., when bracket 120 is in the first position, or the second position). Referring to the example depicted in inset 160, which depicts common reference axes discussed herein, under conditions where bracket 120 is in the third position and where beamformer 108 is coupled to bracket 120, a top face 405 of beamformer 108 may be substantially parallel to the y axis. While not explicitly illustrated at FIG. 4A, a first bracket connector (e.g., first bracket connector 140a at FIG. 2B) may be engaged with a second carrier connector (e.g., second female carrier connector 204 at FIG. 2A), and a second bracket connector (e.g., second bracket connector 140 at FIG. 2B) may be engaged with a first carrier connector (e.g., first female carrier connector 202 at FIG. 2A), in order for bracket 120 to be coupled to carrier 125 in the third position.

At FIG. 4A, in the example embodiment probe cable 110 is shown coupling probe 109 and probe cable attachment connector 170. When bracket 120 is in the third position as depicted, and beamformer 108 is coupled to bracket 120, probe cable 110 may be coiled in the manner shown in order to facilitate compact carrying ability or storage of portable ultrasound machine system 115. Specifically, carrier 125 may include a third probe cable groove 410 created by at least a portion of probe holder 152, and a ridge 412 of carrier 125 along a top of carrier 125, where a shape of the ridge (e.g., concave with respect to its inner face and convex with respect to its outer face, where the inner face corresponds to the inner face 201 of carrier 125) can create a greater amount of space between probe holder 152 and carrier 125 than would otherwise exist if ridge 412 were not configured in the particular shape. Third probe cable groove 410 may be further created by at least a portion of probe 109 itself, with probe 109 acting as a barrier to probe cable movement on one side and the ridge 412 serving as a barrier to probe cable movement on another side of the probe cable. Third probe cable groove 410 in the embodiment depicted at FIG. 4A is of a sizing to enable one winding of probe cable 110 through; however, in other examples the probe cable groove may be of a greater sizing to enable more than one winding of a probe cable, in a case where the probe cable is longer than the probe cable depicted at FIG. 4A, for example. As depicted, probe cable 110 may be further secured by winding probe cable 110 through first probe cable groove 264 and second probe cable groove 267 (refer to the discussion at FIG. 2B). In some examples, one or more input/output ports 420 of beamformer 108 and one or more input/output ports 425 of computing device 107 may together define a fourth groove or space 430 (fourth probe cable groove) by which probe cable 110 may be wound between, for further securing of the probe cable.

FIG. 4A also illustrates in greater detail aspects of probe holder 152, according to various embodiments. Specifically, depicted is a first finger 441, second finger 442, and third finger 443. It may be understood that first finger 441 and second finger 442 may be a part of a top portion of probe holder 152, and third finger may be understood to be a part of a bottom portion of probe holder 152. Each of the first finger, second finger and third finger may function to support or secure probe 109 to carrier 125. In some examples, as will be elaborated in greater detail below, one or more of first finger, second finger and third finger may be at least somewhat flexible to accommodate placement of probe 109 into the pocket defined at least in part by probe holder 152. In one particular example, first finger 441 is at least somewhat flexible with respect to probe holder 152, whereas second finger 442 and third finger 443 are less flexible, or inflexible.

Turning to FIG. 4B, depicted is example illustration 450, showing the same depiction of example portable ultrasound machine system 115 as depicted in FIG. 4A from another angle, to further illustrate first probe cable groove 264, second probe cable groove 267, and third probe cable groove 410. For reference, inset 160 depicts the common reference axes used throughout the present disclosure.

Figure 5:
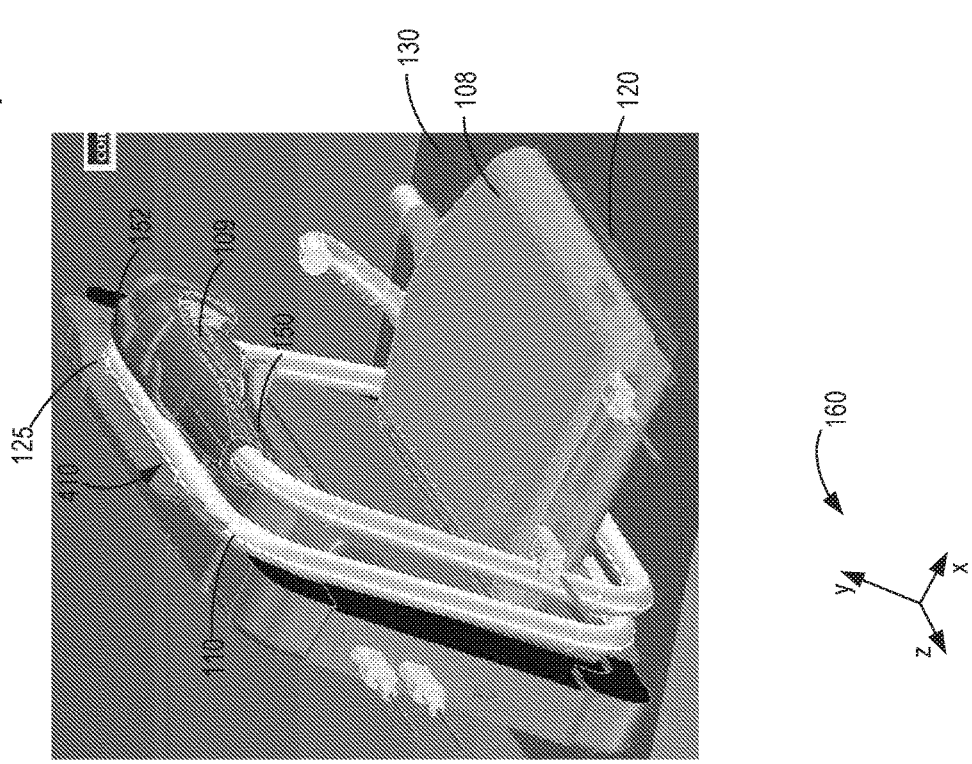
FIG. 5 illustrates the second configuration of the portable ultrasound machine support system of FIG. 3C, also including an ultrasound probe and cable, according to an embodiment.

While FIGS. 4A-4B depict an example of how the probe and probe cable can be stored or arranged under conditions where the bracket is coupled to the carrier in the third position, there may be options for compactly storing the probe and probe cable under conditions where the bracket is coupled to the carrier at either the first position or the second position. Turning to FIG. 5, shown is an illustrative example 500 of how probe 109 and associated probe cable 110 can be stored under circumstances where bracket 120 is in the second position and where usage of the probe is not desired, according to some embodiments. As depicted at FIG. 5, carrier 125 may be coupled to computing device 107, beamformer 108 may be coupled to bracket 120, and bracket 120 may be coupled to carrier 125 in the second position. Probe 109 may be secured by probe holder 152, with at least a portion of probe 109 also supported by the top of carrier handle 150. For compact storage of probe cable 110, the probe cable may be wound underneath bracket 120 between bracket 120 and surface 130 and positioned within third probe cable groove 410, as illustrated. It may be understood that the depiction at FIG. 5 is a representative example and the probe and probe cable may also be stored in similar fashion when bracket 120 is coupled to carrier 125 in the first position.

Figure 6:
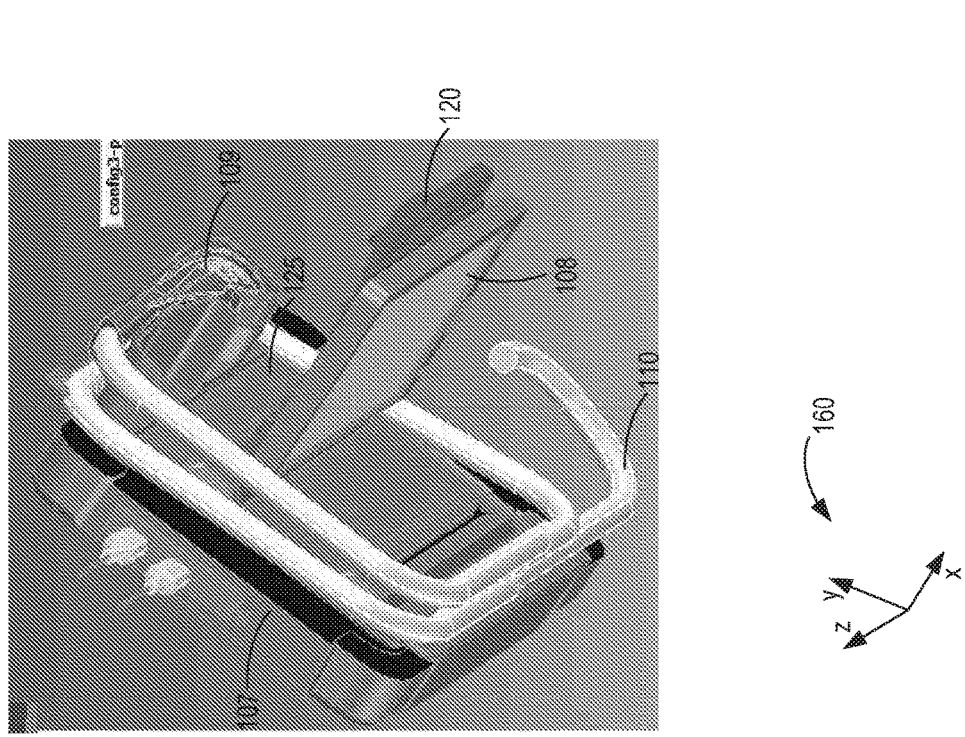
FIG. 6 illustrates another example of the portable ultrasound machine support system of FIG. 1 with a bracket coupled to a computing device, according to an embodiment.

Turning to FIG. 6, depicted is an example illustration 600 showing an embodiment where the beamformer 108 is coupled to the bottom side (e.g., bottom side 252 at FIG. 2B) of bracket 120. Other aspects (e.g., probe 109, computing device 107, carrier 125, and probe cable 110) common to the portable ultrasound machine systems support systems of the present disclosure are labeled but are not discussed in detail here for brevity. Beamformer 108 may be coupled to the bottom side of bracket 120 via a first coupling element (not shown) on a face of the beamformer that is adjacent the bottom side of bracket 120, and a second coupling element (not shown) on the bottom side of bracket 120. As one representative example, the first coupling element may comprise a hook-style fastener while the second coupling element may comprise a loop-style fastener, or vice versa. In another representative example the first coupling element and the second coupling element together may comprise a sliding latch system, similar to the coupling embodiments discussed above with regard to at least FIGS. 2A-2B for coupling the bracket to the carrier. As another representative example the first coupling element and the second coupling element together may comprise a Luer-style system, where the first coupling element comprises a male Luer and the second coupling element comprises a female Luer, or vice versa. Other manners of coupling beamformer 108 to the bottom-side of bracket 120 are within the scope of this disclosure.

In some examples, the first coupling element and the second coupling element may be releasably adhered to the beamformer 108 and/or bottom-side of bracket 120, for example by an adhesive means (e.g., glue, gum, mucilage, paste resin, cement, etc.). In another example, the first coupling element may be adhered to the beamformer 108 by some kind of adhesive means as discussed, but the second coupling element may be integral to the bottom-side of bracket 120. In still other examples, both the first coupling element and the second coupling element may be integral to the beamformer 108 and bottom-side of bracket 120, respectively. As one representative example, the beamformer 108 may be included in a case (not shown) and the case may include the first coupling element either adhered to, or integral to, a side of the case that enables the first coupling element to engage with the second coupling element to attach the beamformer to the bracket.

In still other examples, it may be understood that the first bracket connector (e.g., 140*a*) and second bracket connector (e.g., 140*b*) may be used in addition to or in lieu of any other connector means discussed above, for securing beamformer 108 to the bottom-side of bracket 120. In such an example, female track connectors similar to those discussed above at FIG. 2A may be attached to beamformer 108 in any manner as already discussed, included as part of a case of the beamformer, etc.

Figure 7B:
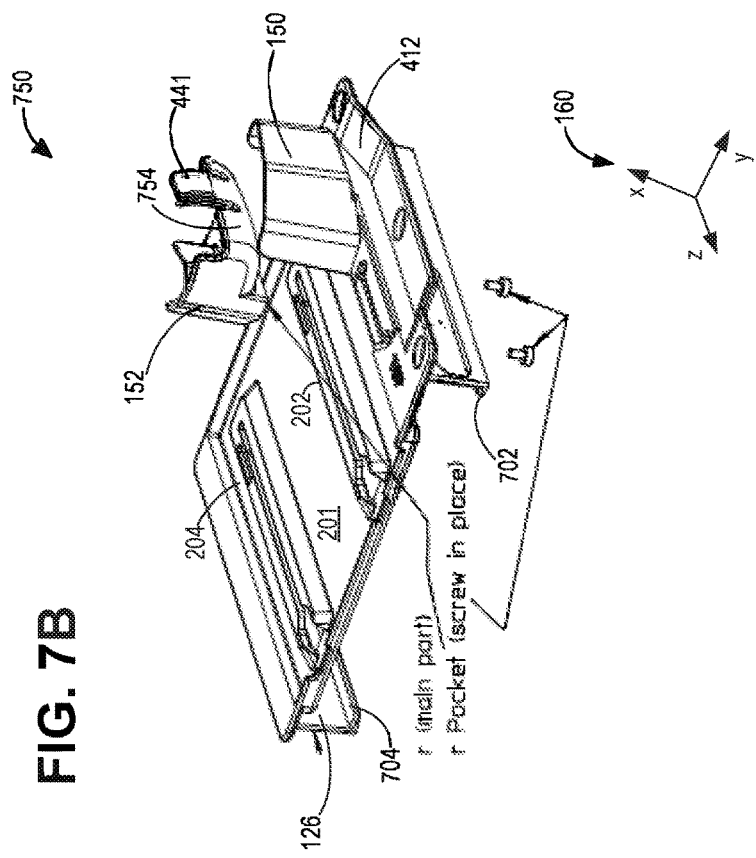
FIG. 7B illustrates an isolated view of the carrier of the portable ultrasound machine system of FIG. 1, according to an embodiment.
Figure 7A:
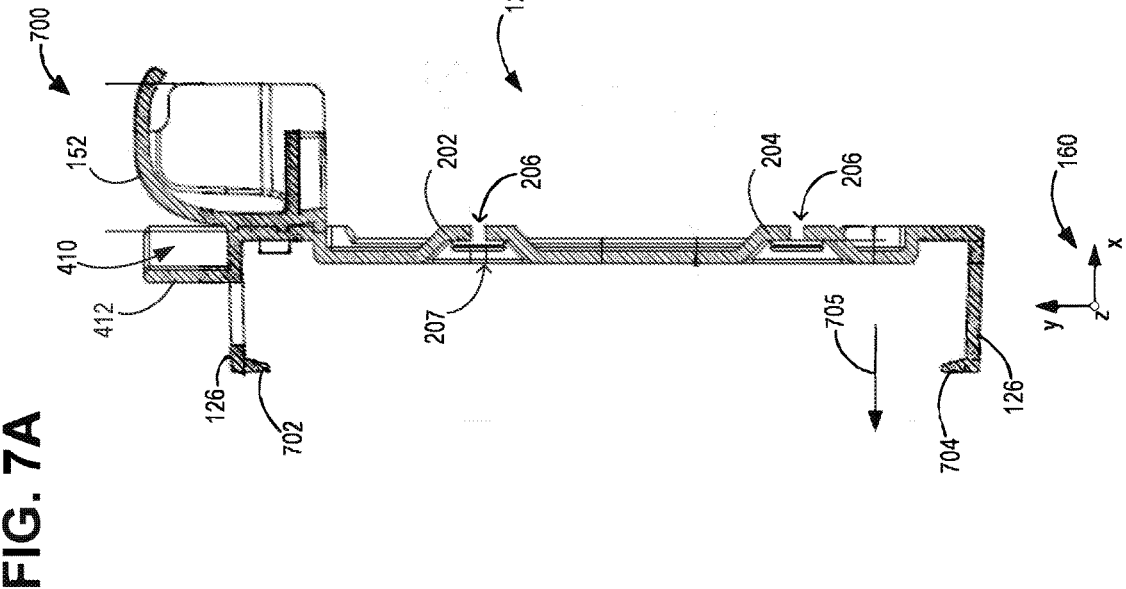
FIG. 7A illustrates a cross-sectional side-view of the carrier of the portable ultrasound machine support system of FIG. 1, according to an embodiment.

FIG. 7A shows illustration 700, depicting a cross-sectional image of an embodiment of carrier 125, viewed along the z axis (refer to inset 160). Illustrated are hooks 126, that protrude along the x-axis and which, as discussed, serve to hold or couple a computing device (e.g., computing device 107 at FIG. 1) to carrier 125. The upper or top hook may include a downward-facing portion 702, and the lower or bottom hook may include an upward-facing portion 704, which may be understood to restrict movement of the computing device in the direction of arrow 705 along the x-axis when the computing device is coupled to carrier 125.

Further depicted is first carrier connector 202 and second carrier connector 204. In this example embodiment, each of first carrier connector 202 and second carrier connector 204 as constructed may include a slit 206 or opening, behind which (e.g., in the direction of arrow 705) may be a void space 207 for receiving a second connector portion (e.g., second connector portion 277 at FIG. 2B) of a T-shaped bracket connector of the present disclosure. As discussed briefly above, it may be understood that dimensions of the second connector portion may be such that the second connector portion cannot pass through slit 206 and in this way, the bracket (e.g., bracket 120 at FIG. 1) may be secured to carrier 125. As discussed above, slit 206 may be for receiving a first connector portion (e.g., first connector portion 276 at FIG. 2B) of the T-shaped bracket connector, thereby enabling the carrier connectors to slidingly receive and release the bracket connector.

While discussed herein is largely in regard to track-style connector systems for securing the bracket to the carrier, other connection means are within the scope of this disclosure including but not limited to Luer-style connector systems, and other mechanical connector systems that are capable of readily engaging and releasing.

Also depicted in the cross-sectional image of the embodiment of carrier 125 at FIG. 7A is a portion of probe holder 152, which as illustrated extends upward along the y-axis beginning from a point below the upper hook 126 and curves in a general shape of the probe (e.g., 109 at FIG. 4A). As discussed, the probe holder 152 may provide a space or pocket in which the probe may be placed when not in use. Still further depicted at FIG. 7A is third grove 410, created by ridge 412 of carrier 125. As elaborated above, third groove 410 may provide a space in which a portion of the probe cable may be positioned, for example when the probe is not in use.

FIG. 7B shows example illustration 750, depicting the example embodiment of carrier 125 in isolation from other components discussed herein. As discussed, carrier 125 may include hooks 126, with upper-facing portion 704 and downward-facing portion 702 shown. Further depicted are first carrier connector 202 and second carrier connector 204. As shown, it may be understood that in this example embodiment (similar to those depicted at FIG. 2A, FIG. 3A, FIG. 3C and FIG. 7A), each of the first carrier connector and the second carrier connector is raised or in other words, extends outward from, inner face 201 along the x axis in order to accommodate the receiving of the generally T-shaped bracket connectors discussed herein. As illustrated, ridge 412 of carrier 125 may extend away from handle 150 along the x axis in the general direction of hooks 126. The ridge formation may contribute to creation of a groove that provides a space for accommodating a portion of the probe cable.

Further shown at FIG. 7B is probe holder 152 separated from carrier 125. Probe holder 152 is depicted as separated from carrier 125 to illustrate that probe holder 152 may comprise a separate piece of carrier 125 that may be screwed into place or otherwise attached, for example. In some examples, probe holder 152 includes a finger 441 that extends from a main body 754 of probe holder 152 and which is bounded on either side by crevices that extend at least a portion into the main body of the probe holder, thereby imparting at least some level of flexibility to finger 441 for enabling the probe to be readily received into probe holder 152, yet also remain secured in the probe holder subsequent to its placement therein.

Proceeding to FIG. 8A, shown is an illustration 800 depicting bracket 120 of the present disclosure in isolation from other components discussed herein (e.g., beamformer, carrier, computing device, etc.). Specifically, illustration 800 shows a top-down view of bracket 120, illustrating a top-face 805 of bracket 120, according to an embodiment. Bracket 120 may include base area 830, defined herein as the region between dashed lines 831 and 832. In some embodiments, on both sides of base area 830 is a shelf, referred to herein as first bracket shelf 807a and second bracket shelf 807b. Each of the first bracket shelf and the second bracket shelf may extend from top-face 805 of base area 830, and as depicted may be slightly elevated along the y axis in relation to top-face 805 of base area 830. Inner lip 255 may extend upward along the y axis from first bracket shelf 807a, perpendicular to first bracket shelf 807a, and outer lip 135 may extend upward along the y axis from second bracket shelf 807b, perpendicular to second bracket shelf 807b.

At a position roughly comprising a mid-point with respect to the z axis of each of inner lip 255 and outer lip 135 are bracket fasteners 810, in some embodiments. Specifically, in this example embodiment, bracket fasteners 810 include a plurality of bracket teeth 811 which extend along the x axis from an elevated aspect (e.g., slightly elevated with respect to a height of the inner lip and the outer lip with respect to the y axis) of each of inner lip 255 and outer lip 135, parallel to top-face 805 of bracket 120. Bracket teeth may extend along the x axis as discussed, but may not extend past each of first bracket shelf 807a or second bracket shelf 807b, as depicted for this example embodiment. Below each of the plurality of bracket teeth 811 may be notches 812. Notches 812 may be understood to comprise depressions in each of first bracket shelf 807a and second bracket shelf 807b (although just the notches for first bracket shelf 807a are visible at FIG. 8A). In some examples, notches 812 may extend through an entirety of the bracket shelves, thereby creating holes or voids in the bracket shelves directly below each of the plurality of bracket teeth. Together the bracket teeth and notches may enable corresponding aspects of a beamformer (e.g., beamformer 108 at FIG. 1) to be releasable engaged with bracket 120 as depicted in, for example, at least FIG. 2B, and FIGS. 3A-4B. Additionally, in some examples one or more bracket ridges 815 may extend upward along the y axis away from top-face 805, which may enhance stability and provide additional contact points and/or support for the beamformer when coupled to bracket 120.

Turning now to FIG. 8B, depicted is an example illustration 850 of bracket 120 as viewed from bottom-face 252. As viewed from the bottom, notches 812 are visible, as in this example embodiment the notches extend through each of first bracket shelf 807a and second bracket shelf 807b. Also visible are each of outer lip 135, inner lip 255, and each of first bracket connector 140a, second bracket connector 140b, third bracket connector 260, and bracket ridges 815. FIG. 8B depicts in greater detail the general "T" shaped configuration of each bracket connector, according to some embodiments. Specifically, depicted for each example bracket connector is first connector portion 276 and second connector portion 277. As depicted, the first connector portion for each of the first bracket connector and the second bracket connector may extend from bottom-face 252 along the y axis, whereas the first connector portion 276 for the third bracket connector 260 may extend along the x axis. Further, the second connector portion 277 for each of the first bracket connector and the second bracket connector as depicted may be substantially parallel to the bottom-face 252, whereas the second connector portion 277 for the third bracket connector may be substantially perpendicular to the bottom-face 252.

Figure 9:
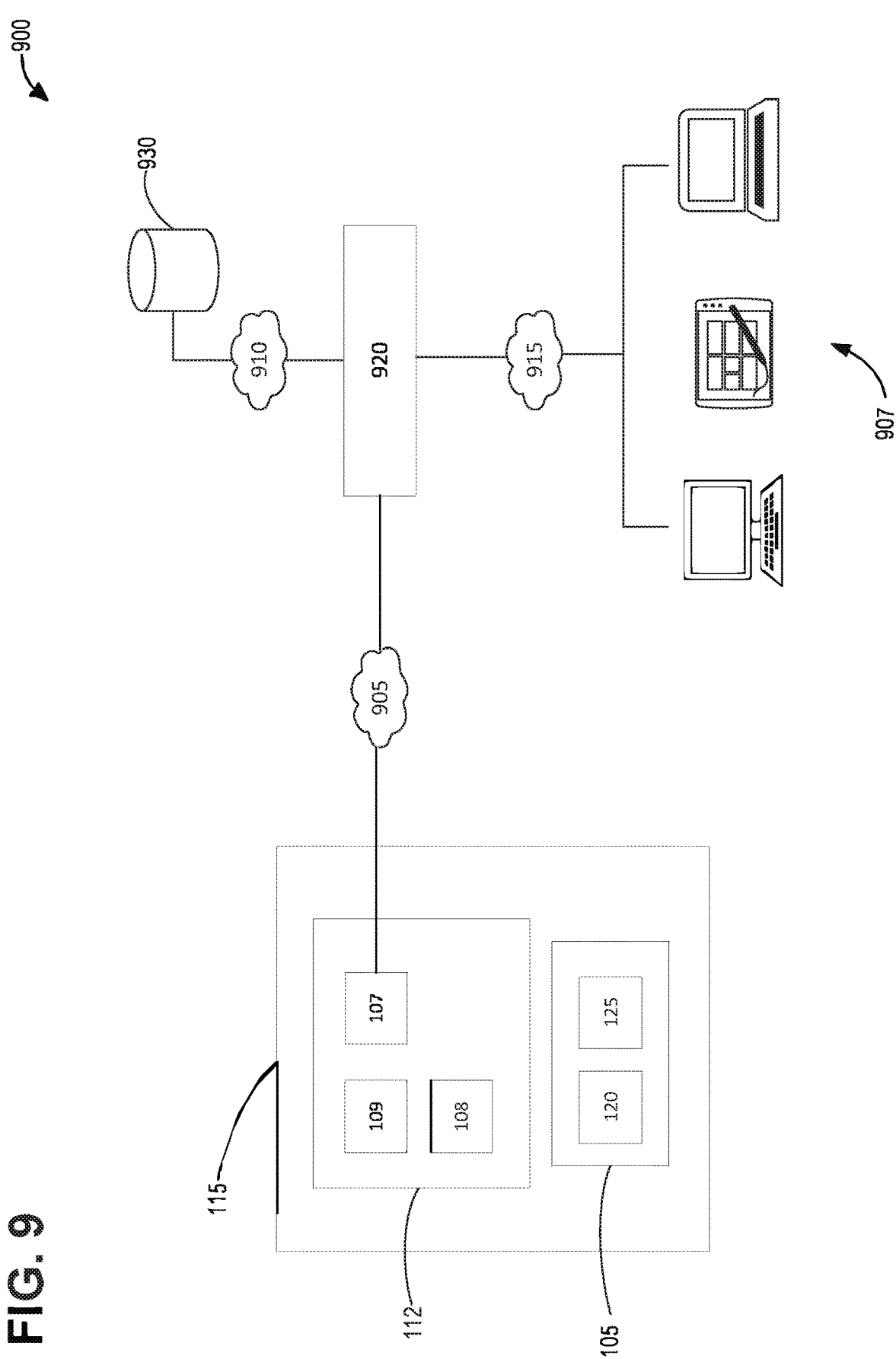
FIG. 9 illustrates an example ultrasound imaging system of the present disclosure, according to an embodiment.

FIG. 9 shows an example illustration of an ultrasound imaging system 900 of the present disclosure. Ultrasound imaging system 900 may include portable ultrasound machine 112, which may comprise probe 109 (and probe cable 110), imaging device 107, and beamformer 108 capable of performing one or more of beamforming and processing, as discussed above.

Ultrasound imaging system 900 further may include portable ultrasound machine support system 105, comprising bracket 120 and carrier 125. Together, as discussed above, portable ultrasound machine 112 and ultrasound machine support system 105 can comprise portable ultrasound machine system 115.

Ultrasound imaging system 900 may further include one or more networks, for example network 905, network 910, and network 915. In some examples one or more of network 905, 910 and 915 may be the same, however in other examples one or more of the networks illustrated may be different from one another, or they may all be different. It may be understood that the illustrated networks may include one or more of a wireless network, a wired network, or a combination of wired and wireless networks. Suitable networks include, but are not limited to, the Internet, a personal area network, a local area network (LAN), a wide area network (WAN) or a wireless local area network (WLAN), for example. Network devices (not shown) may include local area network devices such as routers, hubs, switches, or other computer networking devices.

Depicted is ultrasound imaging server 920. It may be understood that server 920 may comprise a server that is associated with a hospital or other type of facility (e.g., private company) that relies or makes use of ultrasound imaging data. It may be further understood that server 920 may not be limited to just serving ultrasound imaging-related tasks, but in some examples may have additional capabilities, including but not limited to other diagnostic imaging-related tasks.

Also depicted are client device(s) 907. Client devices 907 may be any computing or mobile device, for example laptops, desktops, personal digital assistants (PDAs), desktop computers, and the like. Client device(s) 907 may include a browser or other suitable application configured to access server 920 via a network (e.g., network 915). The client device(s) may include display devices, data storage devices, or other devices that may send data to, and receive data from, server 920. Additional servers may include web servers, for example.

Further illustrated is database 930. It may be understood that database 930 may comprise a data storage devices or devices, including but not limited hard drives, optical storage devices and various other media capable of storing, including, or containing data. As one example, database 930 may be cloud-based.

Via the use of ultrasound imaging system 900, ultrasound images may be acquired by the portable ultrasound machine system, and relayed to the appropriate server via network connectivity, and then images may be viewed or otherwise processed at the terminals by trained operators. Furthermore, obtained images may be stored at the database for future recall or other future diagnostic use or research means.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention is claimed as follows:

1. An apparatus for a portable ultrasound machine, the apparatus comprising:
    a carrier including:
        a first side configured to connect to a computing device, and
        a second side that is opposite the first side, the second side including
            a probe holder,
            a first carrier connector including a first slit, and
            a second carrier connector including a second slit, the first carrier connector positioned to be parallel to the second carrier connector; and
    a bracket configured to connect to a beamformer, the bracket including
        a lip along an edge that is configured to slide into one of the first slit of the first carrier connector or the second slit of the second carrier connector when the bracket is connected to the carrier in a first configuration, and
        a face including two parallel rails that are spaced apart and dimensioned to respectively engage the first and second slits of the first and second carrier connectors when the bracket is connected to the carrier in a second configuration.

2. The apparatus of claim 1, wherein the probe holder includes a handle.

3. The apparatus of claim 1, wherein an underside of the probe holder is formed as a handle.

4. The apparatus of claim 1, wherein an edge of the carrier includes at least one aperture to enable mounting of the apparatus.

5. The apparatus of claim 1, wherein the bracket is configured to releasably connect to the beamformer.

6. The apparatus of claim 1, wherein the bracket is configured to support the carrier for placement in an upright position in the first configuration.

7. The apparatus of claim 1, wherein the first carrier connector is positioned adjacent to a top edge of the carrier and the second carrier connector is positioned adjacent to a bottom edge of the carrier.

* * * * *